(12) United States Patent
Sauska et al.

(10) Patent No.: US 6,824,693 B1
(45) Date of Patent: Nov. 30, 2004

(54) OZONE GENERATOR AND GERMICIDAL DEVICE USING AN ULTRAVIOLET LAMP

(75) Inventors: Christian Sauska, Orange, CT (US); Arpad Pirovic, Woodbridge, CT (US)

(73) Assignee: Light Sources, Inc., Orange, CT (US)

( * ) Notice: Subject to any disclaimer, the term of this patent is extended or adjusted under 35 U.S.C. 154(b) by 155 days.

(21) Appl. No.: 10/140,681

(22) Filed: May 8, 2002

(51) Int. Cl.[7] .............................. C02F 1/32; C02F 1/78; B01J 19/08

(52) U.S. Cl. .................. 210/748; 210/760; 210/192; 210/205; 250/436; 422/24; 422/29; 422/186.07

(58) Field of Search .................. 210/748, 760, 210/764, 192, 198.1, 205; 250/432 R, 436, 437; 422/24, 29, 186.07, 186.12

(56) References Cited

U.S. PATENT DOCUMENTS

| | | | |
|---|---|---|---|
| 4,141,830 A | | 2/1979 | Last |
| 4,230,571 A | | 10/1980 | Dadd |
| 4,274,970 A | * | 6/1981 | Beitzel .................. 210/748 |
| 4,700,101 A | | 10/1987 | Ellner et al. .................. 313/1 |
| 5,230,792 A | | 7/1993 | Sauska et al. .................. 210/97 |
| 5,422,487 A | | 6/1995 | Sauska et al. .................. 250/436 |
| 5,540,848 A | * | 7/1996 | Engelhard .................. 210/748 |
| 5,709,799 A | * | 1/1998 | Engelhard .................. 210/748 |
| 5,779,912 A | * | 7/1998 | Gonzalez-Martin et al. 210/748 |
| 5,942,125 A | * | 8/1999 | Engelhard et al. .......... 210/748 |
| 6,469,308 B1 | * | 10/2002 | Reed .......................... 250/436 |
| 2002/0098109 A1 | * | 7/2002 | Nelson et al. .................. 422/5 |
| 2002/0139756 A1 | * | 10/2002 | Matsuzaki .................. 210/748 |

FOREIGN PATENT DOCUMENTS

| | | | |
|---|---|---|---|
| DE | 195 25 469 A1 | | 1/1997 |
| JP | 04247294 A | * | 9/1992 |
| JP | 08154535 A | * | 6/1996 |
| JP | 10045401 | | 2/1998 |
| JP | 2002224204 | | 8/2002 |
| KR | 2001038518 A | * | 5/2001 |

\* cited by examiner

*Primary Examiner*—Frank M. Lawrence
(74) *Attorney, Agent, or Firm*—Fattibene & Fattibene; Paul A. Fattibene; Arthur T. Fattibene

(57) ABSTRACT

An ultraviolet lamp used for creating ozone. An ultraviolet lamp is enclosed by a container having an inlet at one end and an outlet at the other end. An air flow containing molecular oxygen is created between the container and the ultraviolet lamp. A portion of the wavelength of the ultraviolet lamp is used for generating ozone. Another portion of the wavelength of the ultraviolet lamp is used to kill microorganisms or disinfect a fluid. The ozone generated may be released in the fluid, further purifying and deodorizing the fluid. The present invention combines the germicidal properties of a ultraviolet lamp with the deodorizing properties of ozone in a single device which may be used to purify water or other fluid.

18 Claims, 2 Drawing Sheets

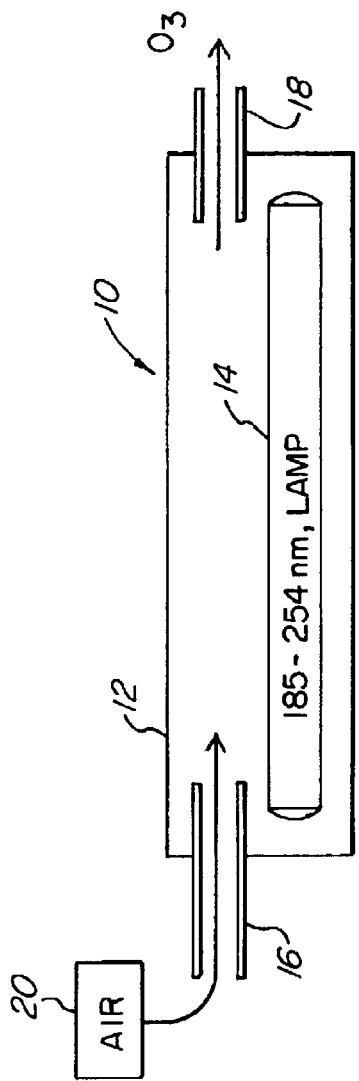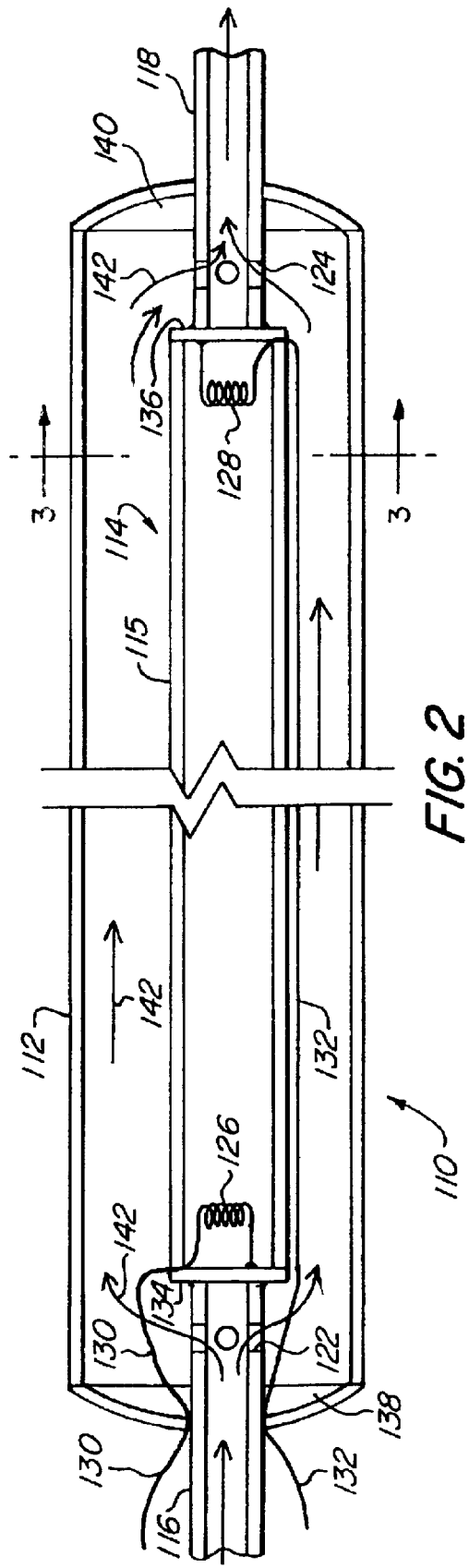

OZONE GENERATOR AND GERMICIDAL DEVICE USING AN ULTRAVIOLET LAMP

FIELD OF THE INVENTION

The present invention relates in general to purifying or disinfecting and deodorizing a fluid, and more particularly to a ultraviolet lamp used as a germicide and to generate ozone.

BACKGROUND OF THE INVENTION

Ultraviolet lamps have been used in germicidal and water purification systems. An ultraviolet water purification system is disclosed in U.S. Pat. No. 5,230,792 entitled "Ultraviolet Water Purification System With Variable Intensity Control" issuing to Sauska et al on Jul. 27, 1993. Therein disclosed is an ultraviolet or UV lamp for generating ultraviolet radiation used to purify a fluid. Another lamp used in water purification systems is in U.S. Pat. No. 4,700,101 entitled "Elongated Tubular Lamp Construction" issuing to Ellner et al on Oct. 13, 1987. Therein disclosed is a tubular gaseous discharge lamp having a wire connected to one electrode extending along the length of the lamp permitting a source of electrical power to be located at one end of the lamp. Therefore, an electrical connection need only be formed along one end of the lamp, which is advantageous in water purification systems.

Another lamp structure for a water purification system is disclosed in U.S. Pat. No. 5,422,487 entitled "Waste Water Purification System With Complementary Interlocking Germicidal Lamp and Socket Construction" issuing to Sauska et al on Jun. 6, 1995. Therein disclosed is a latching and locking pin and socket arrangement for providing a positive mechanical locking preventing any accidental detachment or separation.

Generally, ultraviolet lamps have been used for germicidal and water purification systems because the ultraviolet radiation generated is lethal to simple unicellular organisms or microorganisms, such as algae, bacteria, and protozoa. Typically, ultraviolet radiation between 240 and 320 nanometers is sufficient to kill these microorganisms. Often, other germicidal techniques may have to be utilized to more effectively purify a fluid or water. Additionally, often unpleasant odors are associated with the water being purified.

Ozone has also been utilized in the treatment of drinking water supplies. Odor and taste producing hydrocarbons are effectively eliminated by ozone oxidations. Ozone is a powerful oxidizing allotropic form of the element oxygen. The ozone molecule contains three atoms of oxygen, $O_3$. Additionally, iron and manganese compounds, which discolor water, are diminished by ozone treatment. Compared to chlorine, bacterial and viral disinfection with ozone is considerably more rapid. Generally, the use of ultraviolet radiation or ozone for water purification purposes has been used separately or independently. Accordingly, there is a need for a system that can utilize effectively the beneficial attributes of both ultraviolet radiation and ozone in a fluid or water purification system.

SUMMARY OF THE INVENTION

The present invention can generate ozone as well as use ozone in combination with the germicidal properties of ultraviolet radiation. A tubular ultraviolet lamp is surrounded by a container. An inlet opening at one end of the lamp permits air to flow therethrough between the container and the ultraviolet lamp. Ozone is generated between the ultraviolet lamp and the container and exits at an outlet opening on the other end of the tubular lamp. The ultraviolet lamp produces electromagnetic radiation preferably at wavelengths between 185 and 254 nanometers. In one embodiment of the invention, the container blocks electromagnetic radiation having a wavelength between 185 and 254 nanometers so as to function as an ozone generator. In another embodiment of the invention, the container permits electromagnetic radiation at wavelengths greater than 240 nanometers to pass so as to function as an ozone generator and a germicidal lamp. In a third embodiment of the present invention, the container transmits electromagnetic radiation between 185 and 254 nanometers, resulting in additional generation of ozone around the container and to function as a germicidal lamp.

Accordingly, it is an object of the present invention to generate ozone using an ultraviolet lamp.

It is another object of the present invention to disinfect or germicide and deodorize a fluid.

It is an advantage of the present invention that it has a relatively simple construction and combines germicidal and deodorizing actions in a single device.

It is another advantage of the present invention that it is easily adapted to different applications.

It is a feature of the present invention that a flow of air is directed over an ultraviolet lamp.

It is another feature of the present invention that a predetermined wavelength of an ultraviolet lamp is used to create ozone.

These and other objects, advantages, and features will become readily apparent in view of the following more detailed description.

BRIEF DESCRIPTION OF THE DRAWINGS

FIG. 1 schematically illustrates an embodiment of the present invention.

FIG. 2 is a longitudinal cross section of another embodiment of the present invention.

DETAILED DESCRIPTION OF THE PREFERRED EMBODIMENTS

Figure 3:
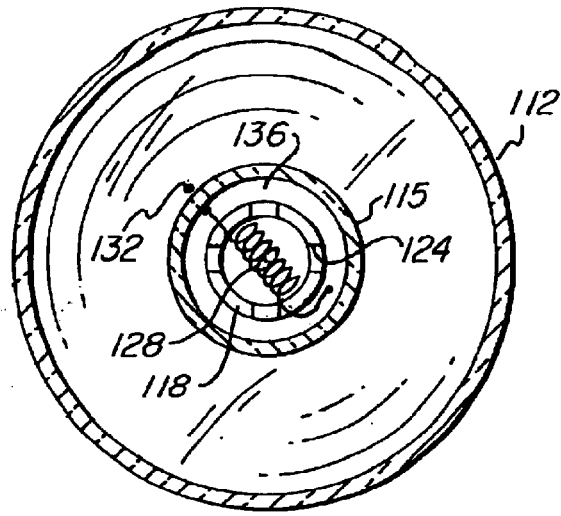
FIG. 3 is a cross section taken along line 3—3 in FIG. 2.

FIG. 1 schematically illustrates the present invention. The ozone generator and germicidal device 10 comprises a container 12 having an ultraviolet lamp 14 placed therein. The ultraviolet lamp 14 generates ultraviolet radiation having a wavelength preferably between 185 and 254 nanometers. An inlet opening 16 is formed at one end of the elongated container 12. An outlet opening 18 is formed within the other end of the elongated container 12. Coupled to the inlet opening 16 is an oxygen or air supply 20. The air supply 20 provides a source of oxygen and creates a gas flow adjacent the ultraviolet lamp 14 between the inlet opening 16 and the outlet opening 18. The ultraviolet radiation, generally ultraviolet radiation having a wavelength below 240 nanometers from the ultraviolet lamp 14, generates ozone between the container 12 and the ultraviolet lamp 14 from the disassociation of molecular oxygen. Ozone, being an oxidizing agent, has a high reduction potential. As a result, ozone will not generally remain ozone for long. Therefore, ozone will only be effectively output from the container 12 when a sufficient gas flow is established between a gap formed between the container 12 and the ultraviolet lamp 14.

For the embodiment illustrated in FIG. 1, to function solely as an ozone generator, the container 12 must block substantially all of the ultraviolet radiation from the ultraviolet lamp 14. Accordingly, no electromagnetic radiation will escape the container 12 and the ultraviolet lamp will be used only to generate ozone from the outlet opening 18. However, the present invention may function as an ozone generator having additional germicidal properties.

In another embodiment of the present invention, the container 12 may be made of a material that passes ultraviolet radiation having germicidal properties and blocks the ultraviolet radiation used in creating ozone. Generally, electromagnetic radiation between the wavelengths of about 185 and 240 nanometers may be used to generate ozone and electromagnetic radiation between the wavelengths of about 240 and 254 nanometers may be used as a germicide to kill simple unicellular organisms or microorganism. Accordingly, in this embodiment, the invention will produce ozone as well as act as a germicidal lamp.

In another embodiment of the present invention, the container 12 may transmit electromagnetic radiation between the wavelengths of about 185 and 254 nanometers. Accordingly, in this embodiment, additional ozone may be created around the container 12 as a result of the transmission of the lower wavelength electromagnetic radiation between the wavelengths of about 185 and 240 nanometers. Therefore, in this embodiment in addition to the creation of ozone between the container 12 and the ultraviolet lamp 14, germicidal properties are obtained by transmitting electromagnetic radiation having wavelengths greater than about 240 nanometers.

FIG. 2 illustrates an embodiment that permits efficient gas flow around an ultraviolet lamp. The ozone generator and germicidal device 110 has a container 112 formed around an ultraviolet lamp 114. Inlet opening 116 extends through a sealed end 138 of the container 112. An end of the inlet opening 116 is attached to an end portion or cap 134 sealing the tubular lamp envelope 115 of the ultraviolet lamp 114. Also attached to the end cap 134 is a lamp electrode 126. One end of the lamp electrode 126 is coupled to an electrode wire 130, which also extends through the sealed end 138. Inlet holes 122 are formed within the tubular inlet opening 116 between the sealed end 138 and the end cap 134.

Similarly, on the other end of the ozone generator and germicidal device 110 is an outlet opening 118. The outlet opening 118 extends through a sealed end 140 and is attached to an end portion or cap 136 attached to the lamp envelope 115 of the ultraviolet lamp 114. Also attached to the lamp envelope 115 is another lamp electrode 128. One end of the lamp electrode 128 is coupled to a wire 132 extending through the lamp envelope 115. The electrode wire 132 extends along the length of the lamp envelope 115 and exits the container 112 through sealed end 138. Accordingly, both electrical connections are at one end of the ozone generator and germicidal device 110. Outlet holes 124 are formed through the tubular outlet opening 118 between the sealed end 140 and the end portion or cap 136 of the ultraviolet lamp 114. Arrows 142 are illustrative of the gas flow longitudinally between the inner surface of the container 112 and the outer surface of the lamp envelope 114 between the inlet holes 122 and the outlet holes 124.

FIG. 3 is a cross section taken along line 3—3 in FIG. 2. The cylindrical container 112 encircles the lamp envelope 115. Attached to the end 136 is the tubular outlet opening 118. Formed within the walls of the tubular opening 118 are outlet holes 124. wire 132 extends along the outside of the lamp envelope 114 and is electrically connected to the lamp electrode 128.

The operation of the device can readily be appreciated while referring to FIGS. 2–3. Air containing molecular oxygen enters the inlet opening 116 and is caused to flow through the inlet holes 122. As illustrated by the arrows 142, the molecular oxygen contained in the air is caused to flow around the lamp envelope 115. Ultraviolet Electromagnetic radiation is generated by the ultraviolet lamp 114 causing the disassociation of molecular oxygen. This results in the formation of ozone or $O_3$. However, since the ozone reacts very quickly, unless the gas flow represented by arrows 142 is sufficient, the ozone generated will convert back to molecular oxygen, $O_2$, before exiting the outlet opening 118 through outlet holes 124. However, once a predetermined flow rate is established, a steady state of ozone creation is obtained. The glass or material of container 112 may be doped using conventional techniques so as to absorb or transmit a predetermined range of wavelengths.

In one embodiment, when the container 112 is made of a material preventing the transmission of electromagnetic radiation, an embodiment is formed that only produces ozone. In another embodiment, when the container 112 is caused to pass wavelengths sufficient to kill simple unicell organisms or microorganisms, for example wavelengths greater than 240 nanometers, an embodiment of the present invention functions as an ozone generator and a germicidal device. In an embodiment in which the container 112 is made from a material that passes all of the wavelengths of electromagnetic radiation, preferably radiation having wavelengths between 185 and 240 nanometers. In this embodiment, additional ozone may be generated as a result of the shorter wavelengths below approximately 240 nanometers transmitted through the container 112 causing additional ozone to be generated. Accordingly, the present invention, in the various embodiments, may be easily adapted to different applications depending upon particular circumstances and the need for ozone generation or germicidal action.

Figure 4:
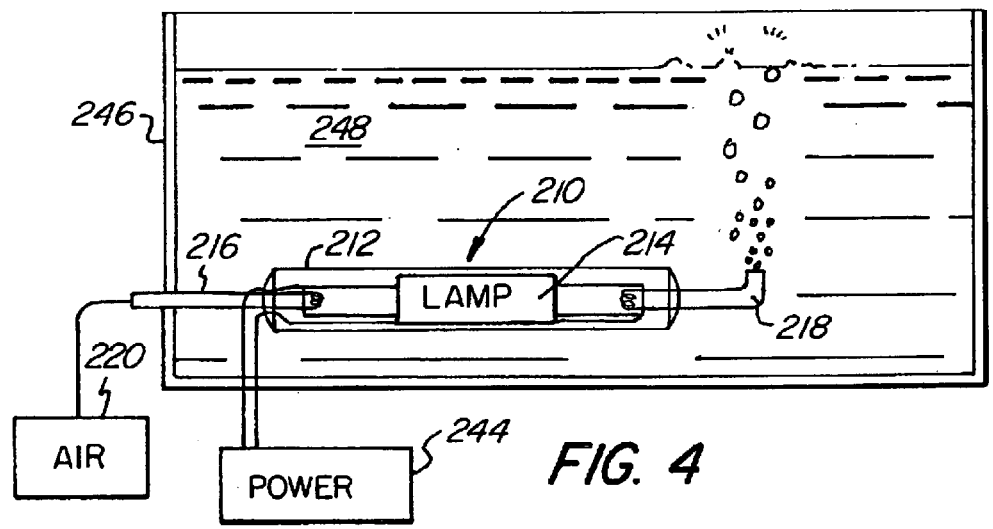
FIG. 4 schematically illustrates an application of the present invention.

FIG. 4 schematically illustrates the application of the present invention to disinfecting a container or tub of water or other fluid. A tub 246 is illustrated, which may be a bathtub, hot tub, swimming pool, waste water treatment container, or any other vessel containing a fluid for purification. The tub 246 contains a fluid to be purified 248. The ozone generator and germicidal device 210 is submerged in the fluid 248. Ultraviolet radiation from the ozone generator and germicidal device 210 effectively kill unicellular and viral organisms or microorganisms. The lamp 214 is powered by a power source 244. The lamp 214 is enclosed in the container 212. An inlet opening 216 communicates with the interior of the container 212. Air supply 220 provides a flow of air to the inlet opening 216 which is caused to provide an air flow around the lamp 214 within the container 212. The air supply 220 may also be any gas containing oxygen for the formation of ozone. The ozone generated from exposure to the ultraviolet electromagnetic radiation generated by the lamp 214 is caused to exit the outlet opening 218 and is released into the water or fluid 248. The ozone helps to additionally purify the fluid or water and acts as a deodorizer. Accordingly, the application of the present invention both germicides and deodorizes a fluid or water.

Figure 5:
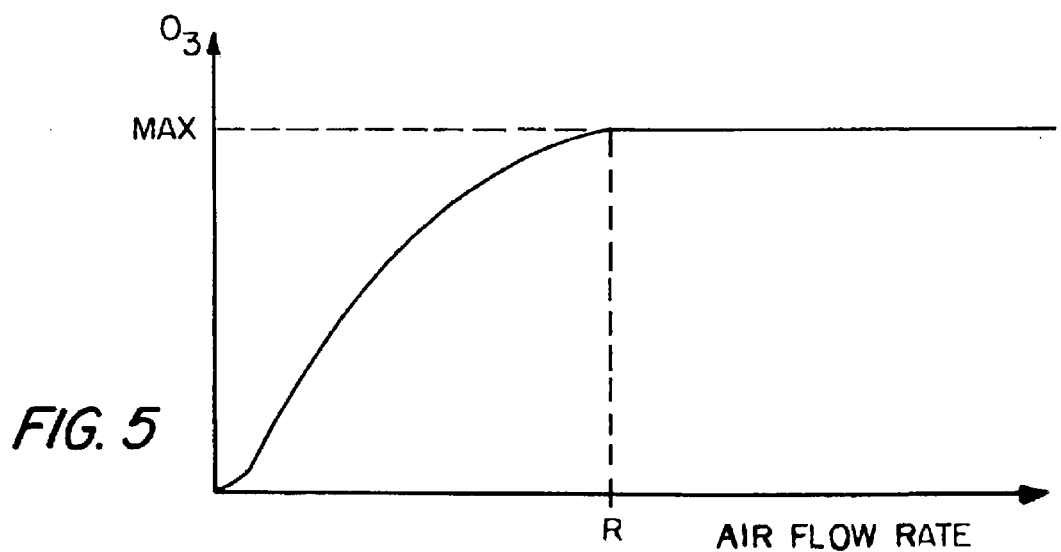
FIG. 5 is a graph illustrating the relationship between the air flow rate and the generation of ozone.

FIG. 5 is a graph illustrating the relationship between the ozone production and the flow rate of air or other gas containing oxygen. The flow rate is indicated on the X-axis or abscissa and the amount of ozone generated is represented on the Y-axis or ordinate. Without a flow rate, none or very little ozone is caused to exit the outlet opening or tube. Upon the initiation of flow, the generation of ozone increases until a predetermined flow rate is achieved, illustrated as R on the X-axis. At this flow rate, a steady state is achieved and a maximum ozone creation is obtained, illustrated as MAX on the Y-axis.

Accordingly, the present invention greatly improves the efficiency of water purification systems in that an ultraviolet lamp having a range of wavelengths effectively uses a portion of the wavelength range to generate ozone and a portion of the wavelength range to kill microorganisms. Accordingly, a water purification system that both destroys germs or and deodorizes is obtained easily and effectively without the need for two different or separate systems.

While the present invention has been illustrated and described with respect to several embodiments, it should be appreciated that various modifications may be made without departing from the spirit and scope of this invention.

What is claimed is:

1. An ozone generator comprising:
    an ultraviolet lamp; and
    a container placed around said ultraviolet lamp having an inlet and an outlet, whereby a gas flow containing oxygen is capable of being established adjacent said ultraviolet lamp, said container made of a material that passes ultraviolet radiation having a wavelength substantially between 240 nanometers and 254 nanometers and blocks ultraviolet radiation having a wavelength substantially between 185 nanometers and 240 nanometers,
    whereby electromagnetic radiation from said ultraviolet lamp causes the disassociation of molecular oxygen in the gas flow forming ozone.

2. An ozone generator as in claim 1 further comprising:
    a supply of gas containing oxygen coupled to the inlet of said container.

3. An ozone generator comprising:
    a tubular container having a first and second sealed end;
    a tubular ultraviolet lamp capable of generating ultraviolet radiation placed within said tubular container and having a first and second end portion;
    a tubular inlet opening attached and extending through the first sealed end of said container and attached to the first end portion of said tubular ultraviolet lamp, said tubular inlet opening having inlet holes therein positioned at a first interior portion between the first sealed end of said tubular container and the first end portion of said tubular ultraviolet lamp; and
    a tubular outlet opening attached and extending through the second sealed end of said container and attached to the second end portion of said tubular ultraviolet lamp, said tubular outlet opening having outlet holes therein positioned at a second interior portion between the second sealed end of said tubular container and the second end portion of said tubular ultraviolet lamp,
    whereby said tubular ultraviolet lamp is suspended within said container and air is capable of being provided to said tubular inlet opening creating an air flow between said container and said tubular ultraviolet lamp generating ozone and causing the ozone to exit said tubular outlet opening.

4. An ozone generator as in claim 3 wherein:
    the ultraviolet radiation has a wavelength between 185 and 254 nanometers.

5. An ozone generator as in claim 3 further comprising:
    a supply of gas containing oxygen coupled to said tubular inlet opening.

6. An ozone generator as in claim 3 wherein:
    said tubular container blocks ultraviolet radiation from said ultraviolet lamp.

7. An ozone generator as in claim 3 wherein:
    said tubular container passes ultraviolet radiation from said ultraviolet lamp having a wavelength sufficient to kill microorganisms.

8. An ozone generator as in claim 7 wherein:
    the wavelength sufficient to kill microorganisms is equal to or greater than 240 nanometers.

9. An ozone generator as in claim 8 wherein:
    the wavelength sufficient to kill microorganisms is within a wavelength range between 240 and 254 nanometers.

10. An ozone generator as in claim 3 wherein:
    said container passes ultraviolet radiation from said ultraviolet lamp having a wavelength sufficient to disassociate oxygen molecules creating ozone.

11. An ozone generator as in claim 10 wherein:
    the wavelength sufficient to disassociate oxygen molecules is equal to or greater than 185 nanometers.

12. An ozone generator as in claim 11 wherein:
    the wavelength sufficient to disassociate oxygen molecules is within a wavelength range between 185 and 240 nanometers.

13. An ozone generator and germicidal device comprising:
    an ultraviolet lamp; and
    a container placed around said ultraviolet lamp having an inlet and an outlet, whereby a gas flow containing oxygen is capable of being established adjacent said ultraviolet lamp and said container is made of a material that transmits electromagnetic radiation having a first wavelength suitable for killing microorganisms, and blocks electromagnetic radiation having a second wavelength suitable for creating ozone,
    whereby the electromagnetic radiation having the second wavelength from said ultraviolet lamp is capable of causing the disassociation of molecular oxygen in the gas flow forming ozone and the electromagnetic radiation having the first wavelength is capable of killing microorganisms.

14. An ozone generator and germicidal device as in claim 13 further comprising:
    a supply of gas containing molecular oxygen coupled to the inlet of said container,
    whereby gas flow containing molecular oxygen is capable of being established between said ultraviolet lamp and said container.

15. An ozone generator as is claim 13 wherein:
    the first wavelength sufficient to kill microorganisms is equal to or greater than 240 nanometers.

16. An ozone generator as is claim 15 wherein:
    the first wavelength sufficient to kill microorganisms is within a wavelength range between 240 and 254 nanometers.

17. A method of purifying and deodorizing water comprising the steps of:
    placing a container under water;

placing an ultraviolet lamp within said container;

establishing a gas flow containing molecular oxygen between said container and said ultraviolet lamp;

generating ultraviolet radiation with said ultraviolet lamp, whereby ozone is created between said container and said ultraviolet lamp;

blocking transmission of the ultraviolet radiation having a wavelength substantially between 185 nanometers and 240 nanometers through the container;

transmitting the ultraviolet radiation having a wavelength substantially between 240 nanometers and 254 nanometers through the container;

releasing the ozone from the container into the water, whereby the water is deodorized; and exposing the water to the ultraviolet radiation, whereby microorganisms are killed purifying the water.

18. A substantially self-contained submersible ozone generator comprising:

a tubular container having a first and second sealed end adapted to be completely submerged in a fluid;

a tubular ultraviolet lamp capable of generating ultraviolet radiation placed within said tubular container and having a first and second end portion;

a tubular inlet opening attached to and extending through the first sealed end of said tubular container, said tubular inlet opening having an inlet hole therein positioned at a first interior portion between the first sealed end of said tubular container and the first end portion of said tubular ultraviolet lamp; and a tubular outlet opening attached to and extending through the second sealed end of said tubular container, said tubular outlet opening having an outlet hole therein positioned at a second interior portion between the second sealed end of said tubular container and the second end portion of said tubular ultraviolet lamp, whereby said tubular ultraviolet lamp is held within said container and air is capable of being provided to said tubular inlet opening creating an air flow between said tubular container and said tubular ultraviolet lamp generating ozone and causing the ozone to exit said tubular outlet opening into the fluid and said tubular container and said tubular ultraviolet lamp are capable of being completely submerged in the fluid.

* * * * *